(12) United States Patent
Rowley et al.

(10) Patent No.: US 11,369,628 B2
(45) Date of Patent: Jun. 28, 2022

(54) CRANBERRY-DERIVED COMPOSITIONS FOR POTENTIATING ANTIBIOTIC EFFICACY AGAINST BACTERIAL PERSISTENCE

(71) Applicant: Rhode Island Council on Postsecondary Education, Warwick, RI (US)

(72) Inventors: David Rowley, Wakefield, RI (US); Jiadong Sun, Narragansett, RI (US); Robert Deering, Wakefield, RI (US); Navindra Seeram, Charlestown, RI (US); Paul Cohen, Narragansett, RI (US)

(73) Assignee: University of Rhode Island Board of Trustees, Kingston, RI (US)

( * ) Notice: Subject to any disclaimer, the term of this patent is extended or adjusted under 35 U.S.C. 154(b) by 0 days.

(21) Appl. No.: 16/498,359

(22) PCT Filed: Mar. 27, 2018

(86) PCT No.: PCT/US2018/024623
§ 371 (c)(1),
(2) Date: Sep. 26, 2019

(87) PCT Pub. No.: WO2018/183369
PCT Pub. Date: Oct. 4, 2018

(65) Prior Publication Data
US 2020/0179434 A1 Jun. 11, 2020

Related U.S. Application Data

(60) Provisional application No. 62/477,393, filed on Mar. 27, 2017.

(51) Int. Cl.
| | | |
|---|---|---|
| A61K 31/716 | (2006.01) | |
| A61P 13/02 | (2006.01) | |
| A61P 31/04 | (2006.01) | |
| A61K 9/06 | (2006.01) | |
| A61K 9/14 | (2006.01) | |
| A61K 31/407 | (2006.01) | |
| A61K 31/43 | (2006.01) | |
| A61K 31/496 | (2006.01) | |
| A61K 31/65 | (2006.01) | |
| A61K 31/7036 | (2006.01) | |
| A61K 31/7048 | (2006.01) | |

(52) U.S. Cl.
CPC .......... *A61K 31/716* (2013.01); *A61K 9/06* (2013.01); *A61K 9/14* (2013.01); *A61K 31/407* (2013.01); *A61K 31/43* (2013.01); *A61K 31/496* (2013.01); *A61K 31/65* (2013.01); *A61K 31/7036* (2013.01); *A61K 31/7048* (2013.01); *A61P 13/02* (2018.01); *A61P 31/04* (2018.01)

(58) Field of Classification Search
CPC ... A61K 31/716; A61K 31/407; A61K 31/496
See application file for complete search history.

(56) References Cited

U.S. PATENT DOCUMENTS

| | | |
|---|---|---|
| 6,423,329 B1 | 7/2002 | Sine et al. |
| 2003/0086986 A1 | 5/2003 | Bruijn et al. |
| 2003/0161897 A1 | 8/2003 | Shanbrom |
| 2007/0196519 A1 | 8/2007 | Royds |
| 2010/0028468 A1 | 2/2010 | Pacioretty et al. |
| 2010/0028469 A1 | 2/2010 | Alberte et al. |
| 2010/0184013 A1 | 7/2010 | Crawford et al. |
| 2010/0330054 A1 | 12/2010 | Priest et al. |
| 2013/0316025 A1* | 11/2013 | Hotchkiss ............. A23L 33/105 424/732 |
| 2018/0360898 A1* | 12/2018 | Tufenkji ................ A61K 31/65 |

FOREIGN PATENT DOCUMENTS

WO 2004047847 A1 6/2004

OTHER PUBLICATIONS

Komae (Agricultural and Biological Chemistry, 54:6, 1477-1484, 1990).*
S. Hemaiswarya et al., "Synergism between natural products and antibiotics against infectious diseases" Phytomedicine (2008) 15:639-652.
E. Pappas and K. M. Schaich, "Phytochemicals of Cranberries and Cranberry Products: Characterization, Potential Health Effects, and Processing Stability," Critical Reviews in Food Science and Nutrituion, (2009) 49:741-781.
ISA/RU "Written Opinion of the International Searching Authority," (2018) PCT/US2018/024623 of which the present application is a national stage filing.
J. Sun et al., "Cranberry (*Vaccinium macrocarpon*) oligosaccharides decrease biofilm formation by uropathogenic *Escherichia coli*," Journal of Functional Foods (2015) 17:235-242.
M. Leatham-Jensen et al., "Uropathogenic *Escherichia coli* Metabolite-Dependent Quiescence and Persistence May Explain Antibiotic Tolerance during Urinary Tract Infection," mSphere (2016) vol. 1 (1): e00055-15.

* cited by examiner

*Primary Examiner* — Pancham Bakshi
(74) *Attorney, Agent, or Firm* — Milstein Zhang & Wu LLC; Duan Wu, Esq.

(57) ABSTRACT

The present invention provides compositions derived from cranberry including xyloglucan and pectic oligosaccharides, and iridoid terpene glycosides. These compositions can be used in conjunction with antibiotics to synergistically kill bacterial persister cells and inhibit bacterial quiescent phenotypes, thereby improving treatment outcomes in recurrent and other infections.

12 Claims, 11 Drawing Sheets

CRANBERRY-DERIVED COMPOSITIONS FOR POTENTIATING ANTIBIOTIC EFFICACY AGAINST BACTERIAL PERSISTENCE

CROSS-REFERENCE TO RELATED APPLICATIONS

This application is a national phase application under 35 U.S.C. 371 of international application PCT/US2018/024623, filed Mar. 27, 2018, which claims priority to and the benefit of U.S. provisional patent application Ser. No. 62/477,393, filed Mar. 27, 2017, which application is incorporated herein by reference in its entirety.

FIELD OF INVENTION

The present invention relates to plant-based extracts, derivatives and therapeutics useful in combating microbes, and methods of making and use thereof. More specifically, the invention relates to compositions derived from cranberry and closely related plants, the compositions including a group of oligosaccharides comprising xyloglucan and pectic oligosaccharides, and co-eluting iridoid terpene glycosides. These compositions can be used with antibiotics to synergistically eradicate bacterial persister cells and inhibit bacterial quiescent phenotypes to thereby improve treatment outcomes in persistent or recurrent infections.

BACKGROUND

The treatment of infectious disease has become more complicated with the emergence of antibiotic resistance, chronic infections, and patients with immunocompromised states such those receiving cancer chemotherapy and those with AIDS. One area of increasing research importance in the treatment of bacterial infection is the phenomenon of persistence. Persistence, or "persister cells," is a dormant state of bacteria that is characterized by a high tolerance to antibiotics. After treatment with an antibiotic, the majority of a population of bacteria is killed, but a small subpopulation that show little or no cell division, called persister cells, often remains. The difference between persistence and antibiotic resistance is: persister cells that remain after an initial antibiotic treatment can be cultured or otherwise induced out of their dormant state; once they are treated again with the same antibiotic, these former persister cells can be killed, whereas resistant cells would not. Increases and decreases in persistence can be induced by a variety of stimuli including media containing different carbon sources and application of certain antibiotics (see Amato & Brynildsen, 2014, *PLoS One*, 9(3), e93110; Keren, I., et al., 2012, *Methods Enzymol*, 517, 387-406; and Kotte, O., et al., 2014, *Mol Syst Biol*, 10(7), 736). Bacterial persister cells are strongly implicated in the pathology of difficult-to-treat infections such as recurrent Urinary Tract Infections (UTIs), tuberculosis, and biofilm associated infections such as those in cystic fibrosis.

Persister cells are reminiscent of quiescent intracellular reservoirs (QIRs) that are formed during UTIs. Upon infecting transitional urothelial cells in the bladder, uropathogenic *Escherichia coli* (UPEC) cells can enter a non-growing "quiescent" state, also known as QIRs. These QIRs can reactivate at later times, and are thought to be reservoirs for causing recurrent infections. Molecules that can prevent QIRs are therefore a potential adjunctive therapy to prevent and treat UTIs.

Cranberry (*Vaccinium macrocarpon*) products have been extensively researched for their role in the treatment and prevention of UTIs. Phytochemical analyses of cranberry in the past have mainly focused on small molecular structural classes such as proanthocyanidins (PACs), flavanols, and triterpenoids, e.g., see U.S. Patent Application 20170028006. There have been studies investigating cell wall complex carbohydrates (oligosaccharides) from cranberry, but they have mostly focused on potential anti-adhesion and anti-biofilm properties, particularly against uropathogenic *E. coli*. See Howell et al., 1998, *N. Engl. J. Med.*, 339:1085-1086; and Lai Yeap Foo et al., 2000, *Phytochemistry*, 54, 173-181. Other research has determined that some small molecules have persister cell-lowering effects in UPEC and *Pseudomonas aeruginosa* (see Allison et al., 2011, *Nature*, 473(7346), 216-220; Bahar et al., 2015, Pharmaceuticals (Basel), 8(4), 696-710; Barraud et al., 2013, *PLoS One*, 8(12), e84220; Pan et al., 2013, *Appl Microbiol Biotechnol*, 97(20), 9145-9154). None of the existing research provides a way to use cranberry-based products or compositions to address recurrent microbial infections that result from persistence in microbes. There had also not been much investigation of cranberry components other than polyphenolics such as PACs.

Accordingly, there exists a need for therapeutic products, preferably derived from a source with little or no toxic side effect on animals and humans, that can eradicate or substantially damage the persister cell population and prevent quiescence in order to prevent or lower the possibility for recurrence of chronic infections. The present invention described below includes the chemical characterization, method of purification, persister cell-lowering effects, and prevention of quiescence by oligosaccharides and associated constituents extracted from or largely derived from cranberries.

SUMMARY OF THE INVENTION

One object of the present invention is to provide chemicals extracted, purified and derived from a plant source, e.g., pectinase-treated American cranberries (*Vaccinium macrocarpon*), and their compositions, where such chemical ingredients (a) significantly lower the persister cell numbers when administered together with antibiotics, or, (b) alter the quiescent phenotype of pathogens to render them susceptible to antimicrobial attacks. In an embodiment of the invention, an oligosaccharide-enriched fraction is co-purified and tested with a series of terpene glycosides, including monotropein. This mixture of cranberry-derived oligosaccharides is hereinafter referred to as "the oligosaccharides of the invention" unless stated to be a specific kind of oligosaccharide.

The second object of the present invention is to provide a method of purification to acquire the oligosaccharides of the invention and other active ingredients by utilizing reverse-phase C18 chromatography and porous graphitized carbon chromatography. Enrichment of the oligosaccharides in cranberry-derived fractionation is nearly synonymous with removal of phenolic compounds, including the type A PACs, considered important by conventional wisdom in terms of potential anti-bacterial benefits. Conversely, a phenolic-enriched (or PACs enriched) fraction is similarly depleted of oligosaccharides, including those identified in previous studies.

The third object of the present invention is to provide a method for preventing and/or treating recurrent infection by co-administration of the oligosaccharides of the invention, as well as other active ingredients including terpene glycosides, with an antibiotic or other antimicrobial regimen to lower or kill pathogenic bacterial persister cells.

According to these objects, in one aspect, the present invention provides an antimicrobial preparation or formulation, comprising at least one composition derived from cranberry (e.g., extracts from pectinase-treated American cranberries or *Vaccinium macrocarpon*), wherein the preparation is capable of, and preferably, effective at making a population of bacterial persister cells susceptible to further antimicrobial, e.g., antibiotic, antiseptic, or disinfectant, treatment. In a feature, such a composition is enriched in at least one or more of the following: a pectic oligosaccharide, a xyloglucan oligosaccharide, and a terpene glycoside. In another feature, the desired ingredient(s) are enriched through a purification process such as chromatography. The preparation can be in a physical state of solid, liquid, gas, semi-solid, semi-liquid or a combination thereof. For example, the preparation can be in the form of a powder, a gel, a vapor, a fluid or a combination thereof. The antimicrobial formulation can be prepared by: first, purification from raw cranberries into a form easy for storage and shipping; and then, combined with a beverage such as a fruit juice which can include a fruit extract other than cranberry or a pharmaceutically acceptable excipient, carrier, or diluent. The antimicrobial formulation can be for external application (e.g., epidermal) or internal consumption.

In a preferred embodiment, the pectic oligosaccharide has at least one "unsaturated" terminal, i.e., with at least one unsaturated carbon bond. In various embodiments, the terpene glycoside comprises an iridoid, e.g., a monotropein. In a preferred embodiment, the terpene glycoside is a 6,7-dihydromonotropein or deacetylasperulsidic acid. In a feature, the antimicrobial preparation or formulation further includes a bactericidal antibiotic, selected from: Aminoglycosides, Penicillins, Cephalosporins, Carbapenems, Fluoroquinolones, Sulfonamides, Macrolides, and Tetracyclines. Further examples of antibiotics that may be included in the preparation include: gentamicin, tobramycin, penicillin, amoxicillin, ampicillin, cephalexin, ciprofloxacin, levofloxacin, ofloxacin, co-trimoxazole, trimethoprim, erythromycin, clarithromycin, azithromycin, tetracycline, and doxycycline.

In an aspect of the invention, a pharmaceutical composition is provided with a composition purified from cranberry, an antibiotic, and a pharmaceutically acceptable excipient, carrier, or diluent. In a feature, the composition purified from cranberry is one or more pectic oligosaccharides. In another feature, the pharmaceutical composition further includes one or more terpene glycosides. The pharmaceutical composition may further include one or more xyloglucan oligosaccharide.

In a further aspect of the invention, a method for reducing a bacteria population is provided where the method includes the steps of:

(a) contacting a population of bacteria with the antimicrobial preparation of the invention to sensitize the population; and (b) simultaneous or subsequent to step (a), contacting the same population of bacteria with an antibiotic.

In yet another aspect of the invention, a method for treating a patient suffering from a pathogenic infection is provided where the method includes the steps of:

(a) administering to a patient a pharmaceutical composition comprising a composition purified from cranberry to sensitize a bacterial population in the patient; and (b) simultaneous or subsequent to step (a), administering to the patient an antibiotic.

In one embodiment, the infection being treated for is UTI, or recurrent UTI. In various embodiments, the infection being treated for is mainly caused by bacteria selected from the group consisting of *Staphylococcus aureus, Escherichia coli, Pseudomonas aeruginosa, Lactobacillus acidophilus*, and *Gardnerella vaginalis*. In one feature, the antibiotic is bactericidal and selected from examples described elsewhere in the present specification.

DETAILED DESCRIPTION OF THE INVENTION

Unless otherwise noted, technical terms are used according to conventional usage. Definitions of common terms in molecular biology may be found, for example, in J. Krebs et al. (eds.), *Lewin's Genes XII*, published by Jones and Bartlett Learning, 2017 (ISBN 9781284104493); Robert A. Meyers (ed.), *Molecular Biology and Biotechnology: a Comprehensive Desk Reference*, published by Anmol Publications Pvt. Ltd, 2011 (ISBN 9788126531783); and other similar technical references.

As used in the specification and claims, the singular form "a", "an", or "the" includes plural references unless the context clearly dictates otherwise. For example, the term "a cell" includes a plurality of cells including mixtures thereof.

As used herein, the term "patient" is intended for a human or non-human mammal affected or likely to be affected with a condition associated with a bacterial infection. Said patient is preferably a human being.

As used herein, the term "enriched" refers to the quality in a preparation, formulation or composition where one or more ingredients' proportions are significantly and artificially increased compared to their respective, natural levels. Enrichment can be achieved through purification or isolation techniques well known to one skilled in the art and include any method that reduces or removes unwanted parts after separation from the desired parts through techniques such as evaporation, precipitation, filtration, distillation, fractionation, and so on.

The present invention provides compositions, formulations, and preparations involving a group of oligosaccharides, as well as iridoid terpene glycosides, all isolated from pectinase-treated cranberry hull using American cranberries (*Vaccinium macrocarpon*) and having persister cell-lowering and UPEC quiescence inhibiting effects. The oligosaccharides of the invention primarily involve two types of oligosaccharides: (a) xyloglucan oligosaccharides, and (b) pectic oligosaccharides. Useful embodiments of the invention include one or both of (a) and (b), with or without terpene glycosides.

In some embodiments, the isolated xyloglucan oligosaccharides are xyloglucan oligomers with degrees of polymerization from 2-mers to 10-mers, and preferably, 6-mers to 10-mers. The xyloglucan oligosaccharides, according to various embodiments of the present invention, have a backbone of 1,4-β-D-glucose and side chains such as X (α-D-Xylp-(1-6)-β-D-Glcp-), S (α-L-Araf-(1-2)-α-D-Xylp-(1-6)-β-D-Glcp-) and L (β-D-Galp-(1-2)-α-D-Xylp-(1-6)-β-D-Glcp-) were detected.

Figure 1:
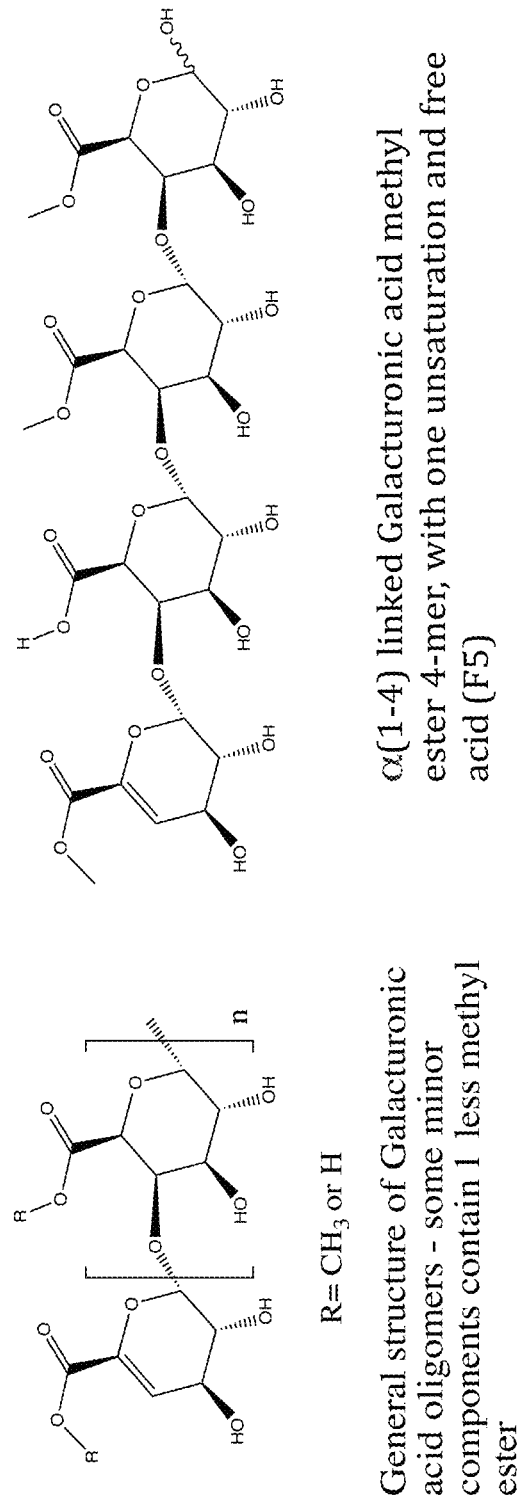
FIG. 1 shows representative structures of the pectic oligosaccharides of the invention. The terminal unit may include unsaturation due to eliminative cleavage by pectic lyases.

The pectic oligosaccharides, according to embodiments of the present invention, are modified oligomers of polygalacturonic acids of molecular sizes ranging from monomers to 8-mers (FIG. 1). In these pectic oligosaccharides, most of the carboxylic acids are methyl esterified and some hydroxyls are acetylated. Some terminal units contain unsaturation characteristic of eliminative cleavage by pectic lyases.

Figure 2:
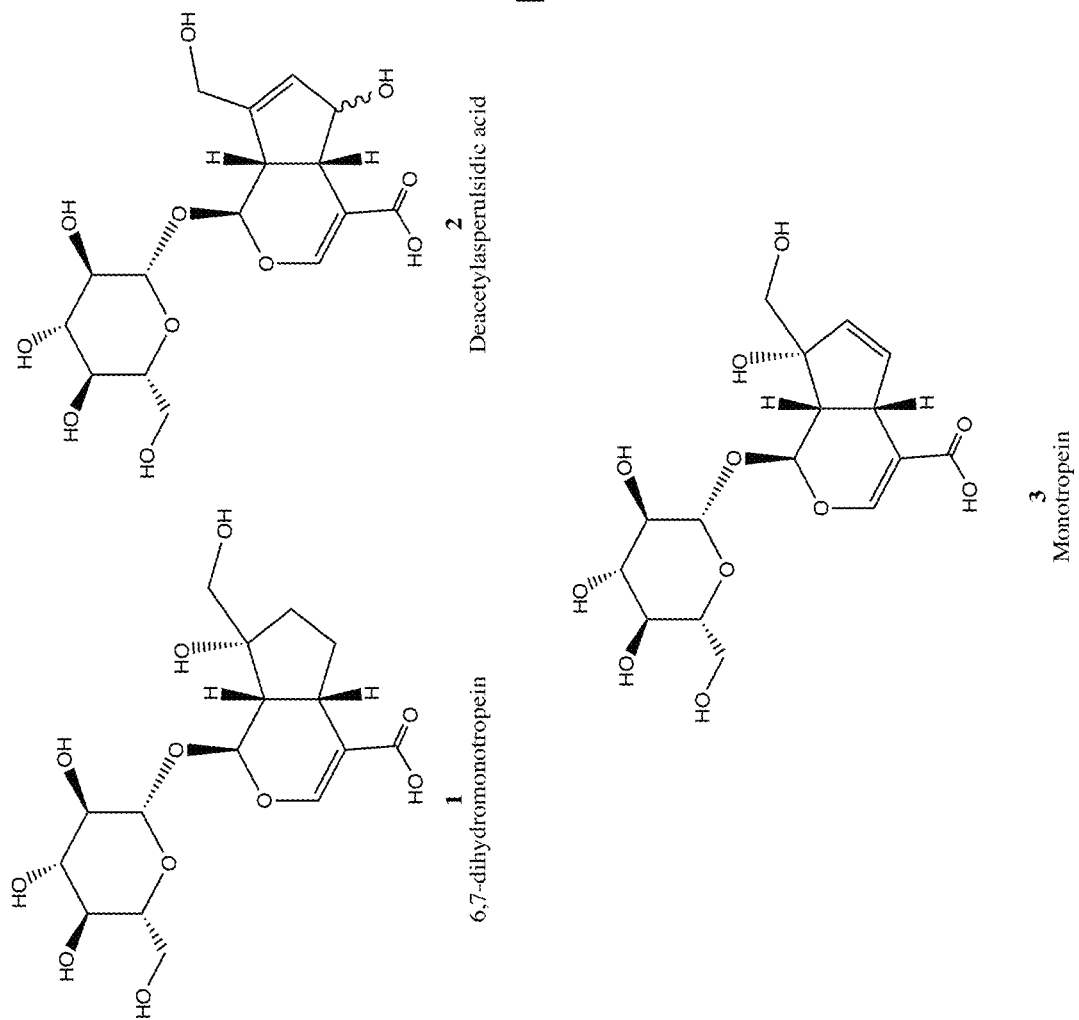
FIG. 2 shows structures of the iridoid type terpene glycosides that co-elute with the pectic oligosaccharides, according to an embodiment of the invention.
Figure 3:
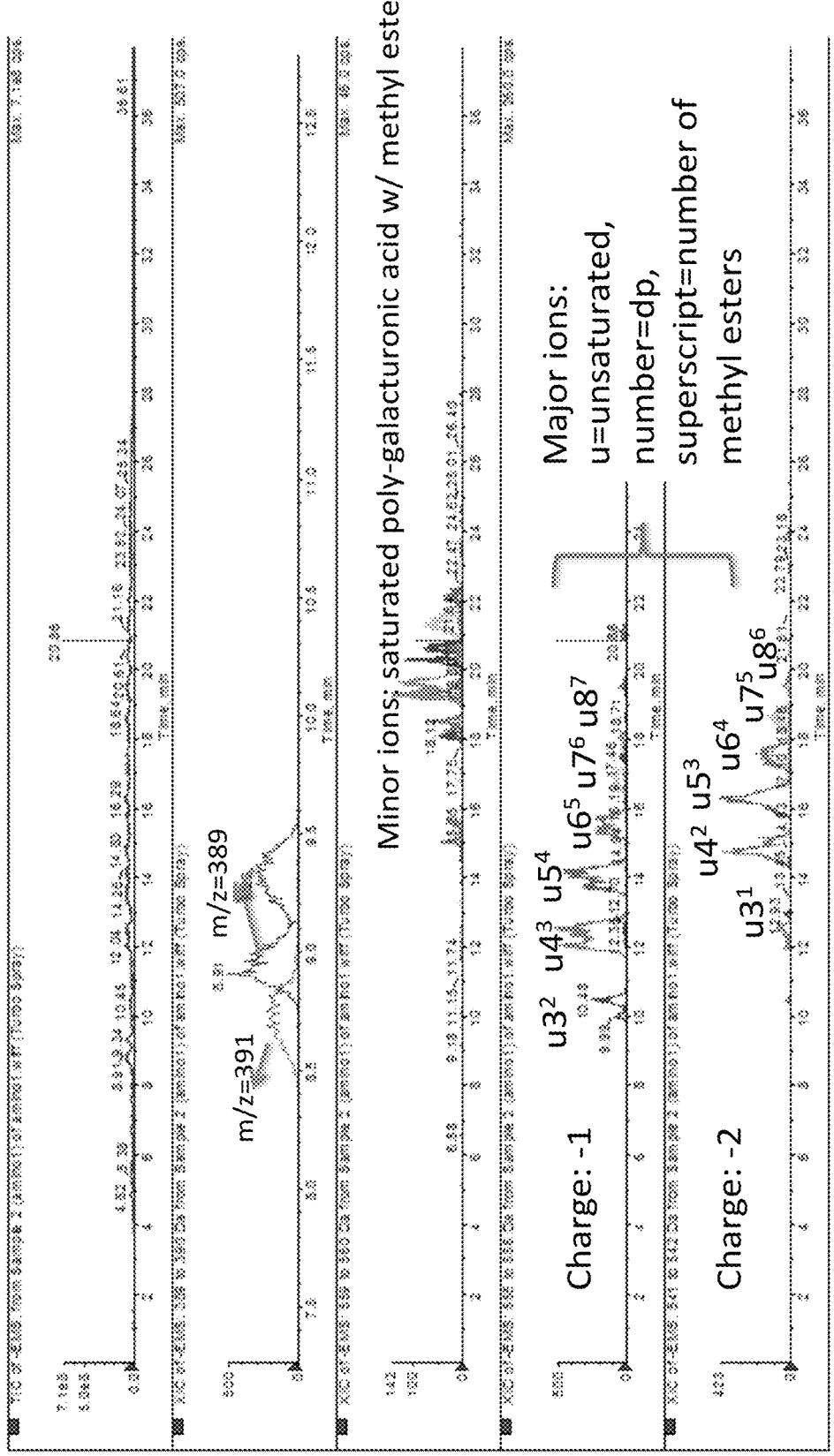
FIG. 3 shows an LC/MS qualitative analysis of the 10% PGC fraction obtained according to an example of the inventive embodiment. The LC/MS chromatogram shows the diversity of molecules contained in the 10% PGC fraction. The mass spectrometry measurements were acquired in the negative ion mode. From top to bottom: Total ion chromatogram; Extract ions of m/z 391 and m/z 389; Extract ions for saturated poly-galacturonic acid methyl esters (DP 3-8); Extract ions for unsaturated poly-galacturonic acid methyl esters (DP 3-8), single free carboxylic acid; and Extract ions for unsaturated poly-galacturonic acid methyl esters (DP 3-8), double free carboxylic acids.
Figure 4:
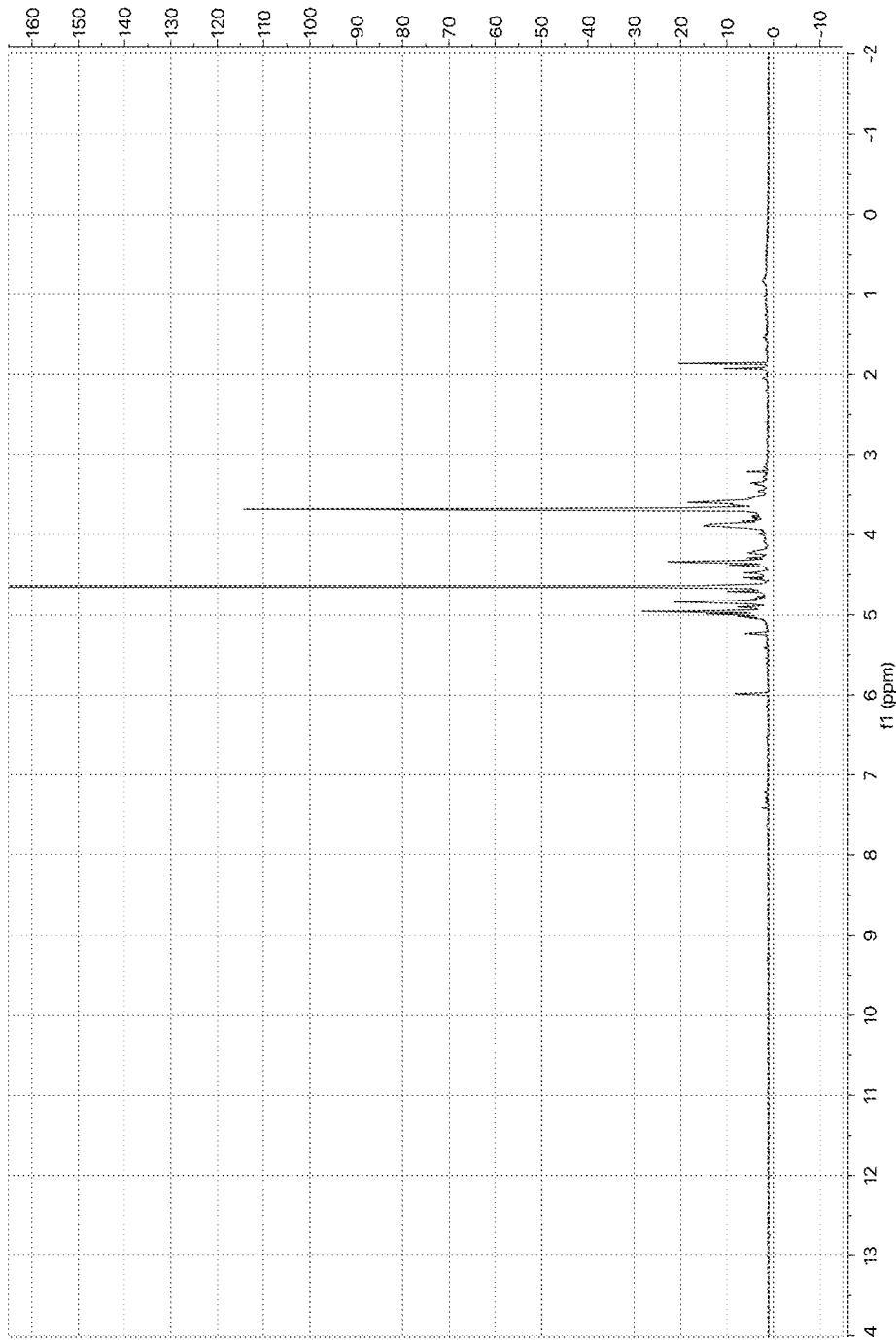
FIG. 4 shows the $^1$H NMR spectrum of PGC 10% fraction (500 MHz, $D_2O$), according to an embodiment of the present invention.
Figure 5:
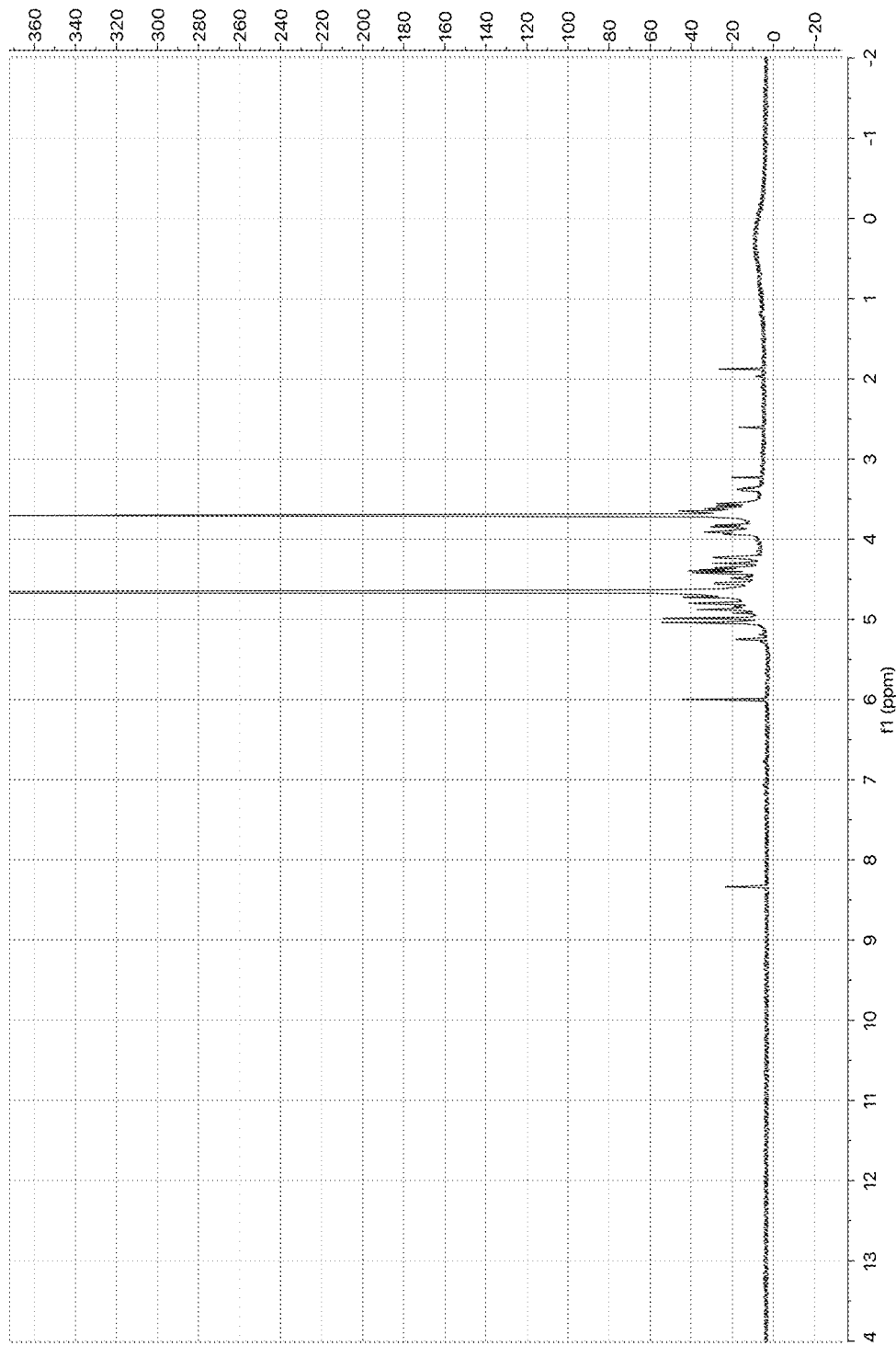
FIG. 5 shows the $^1$H NMR spectrum of pectic oligosaccharide u4$^3$ (500 MHz, $D_2O$), according to an embodiment of the present invention.
Figure 6:
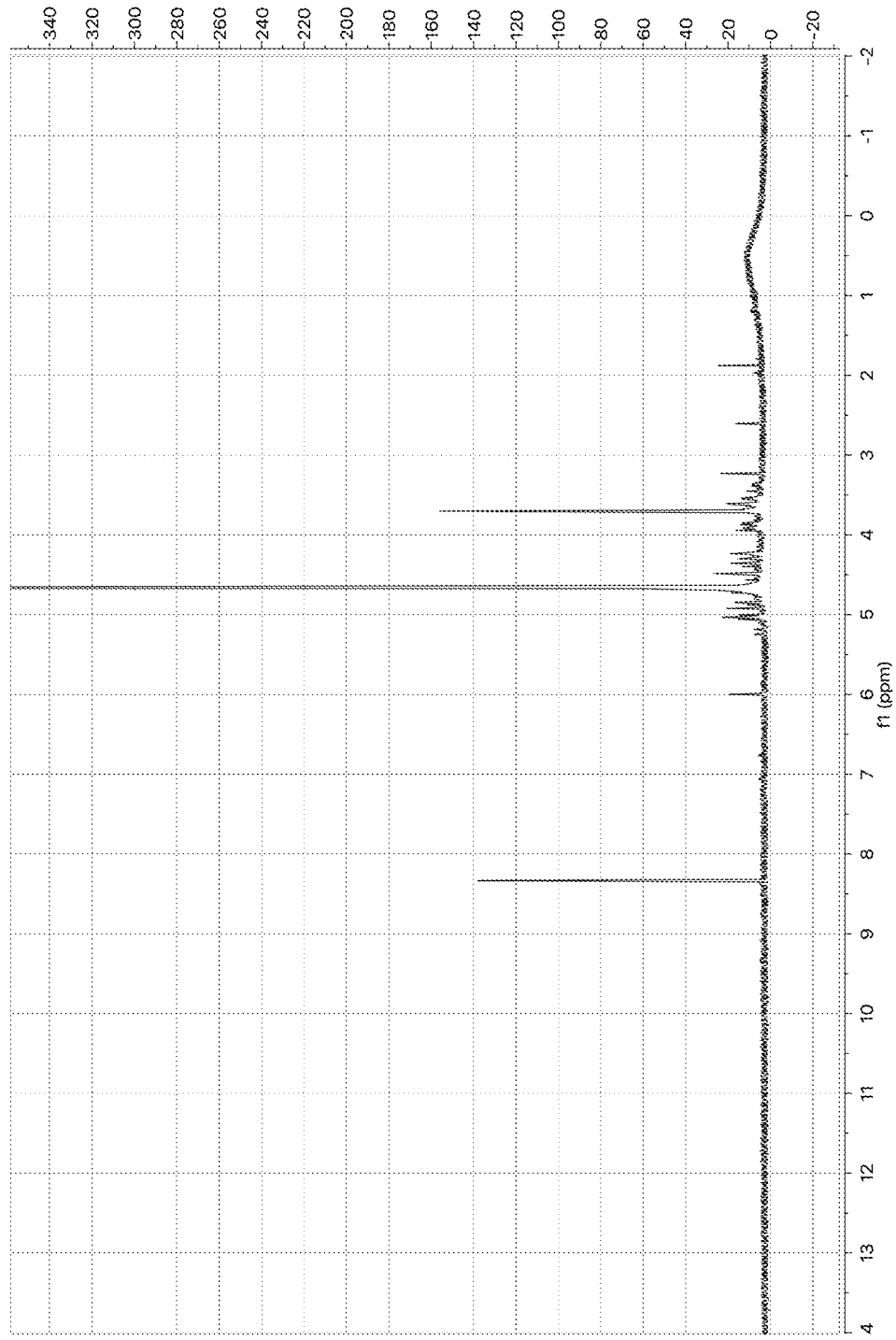
FIG. 6 shows the $^1$H NMR spectrum of pectic oligosaccharide u3$^2$ (500 MHz, $D_2O$), according to an embodiment of the present invention.
Figure 7:
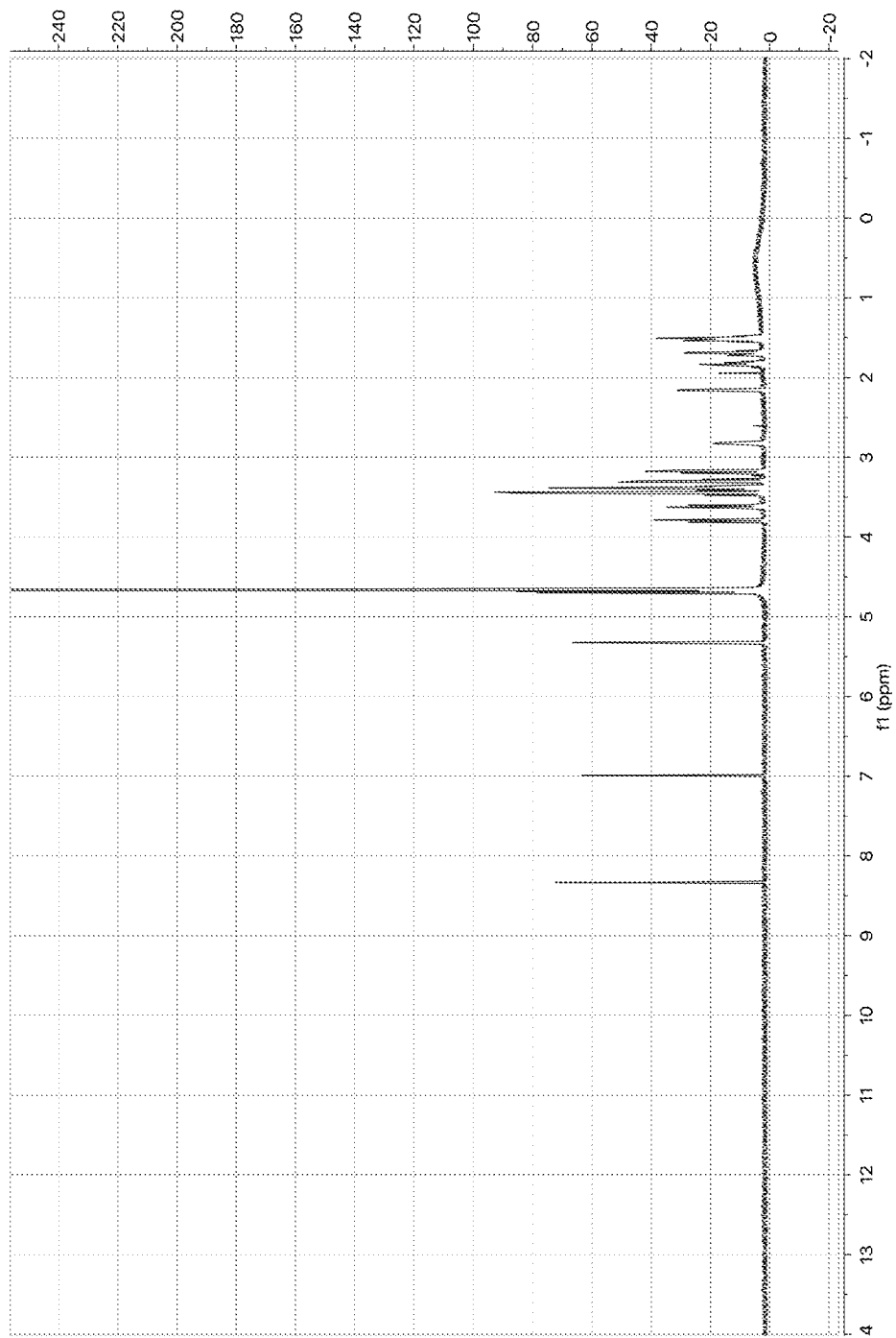
FIG. 7 shows the $^1$H NMR spectrum of iridoid 1 (500 MHz, $D_2O$), according to an embodiment of the present invention.
Figure 8:
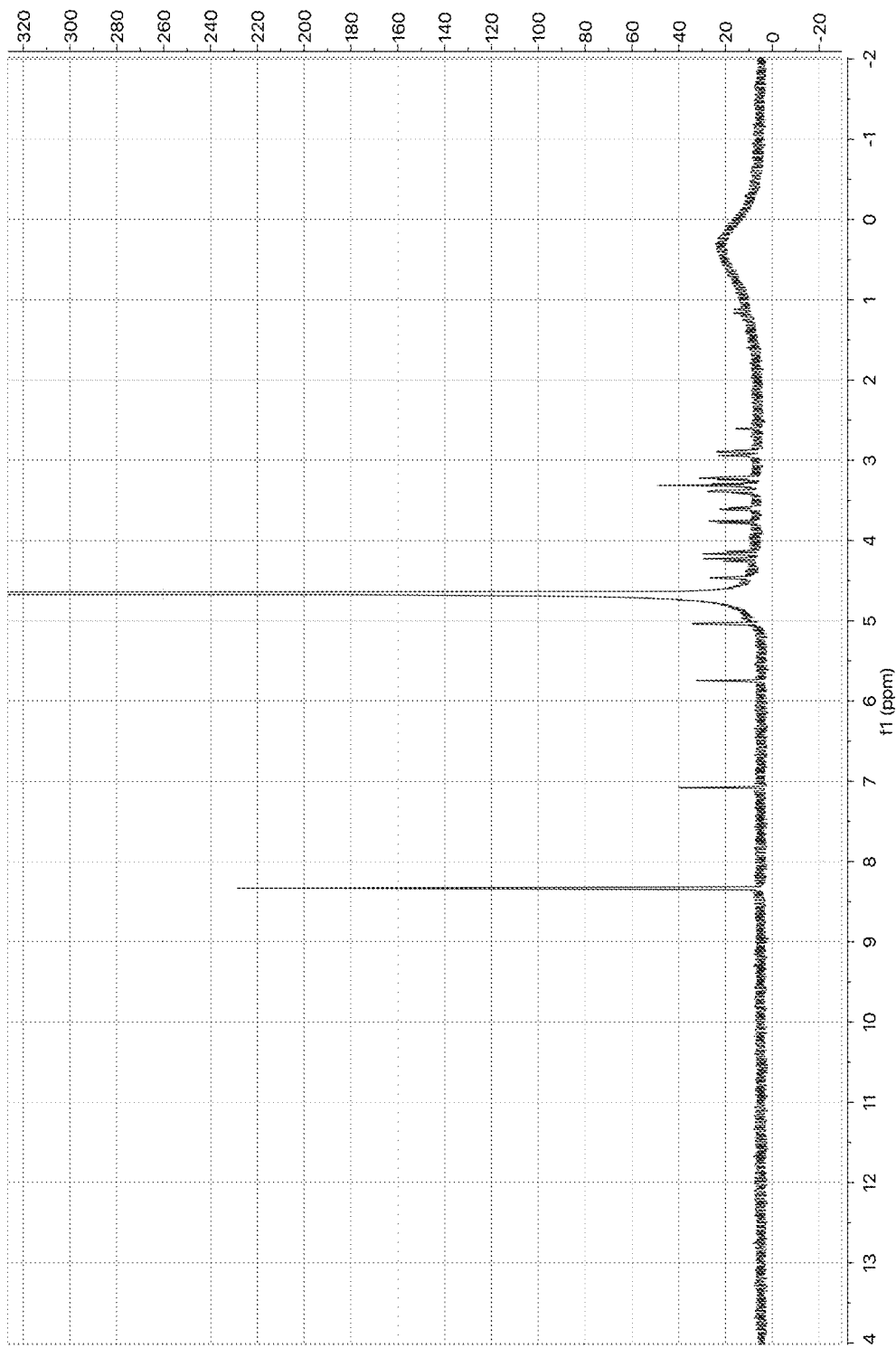
FIG. 8 shows the $^1$H NMR spectrum of iridoid 2 (500 MHz, $D_2O$), according to an embodiment of the present invention.
Figure 9:
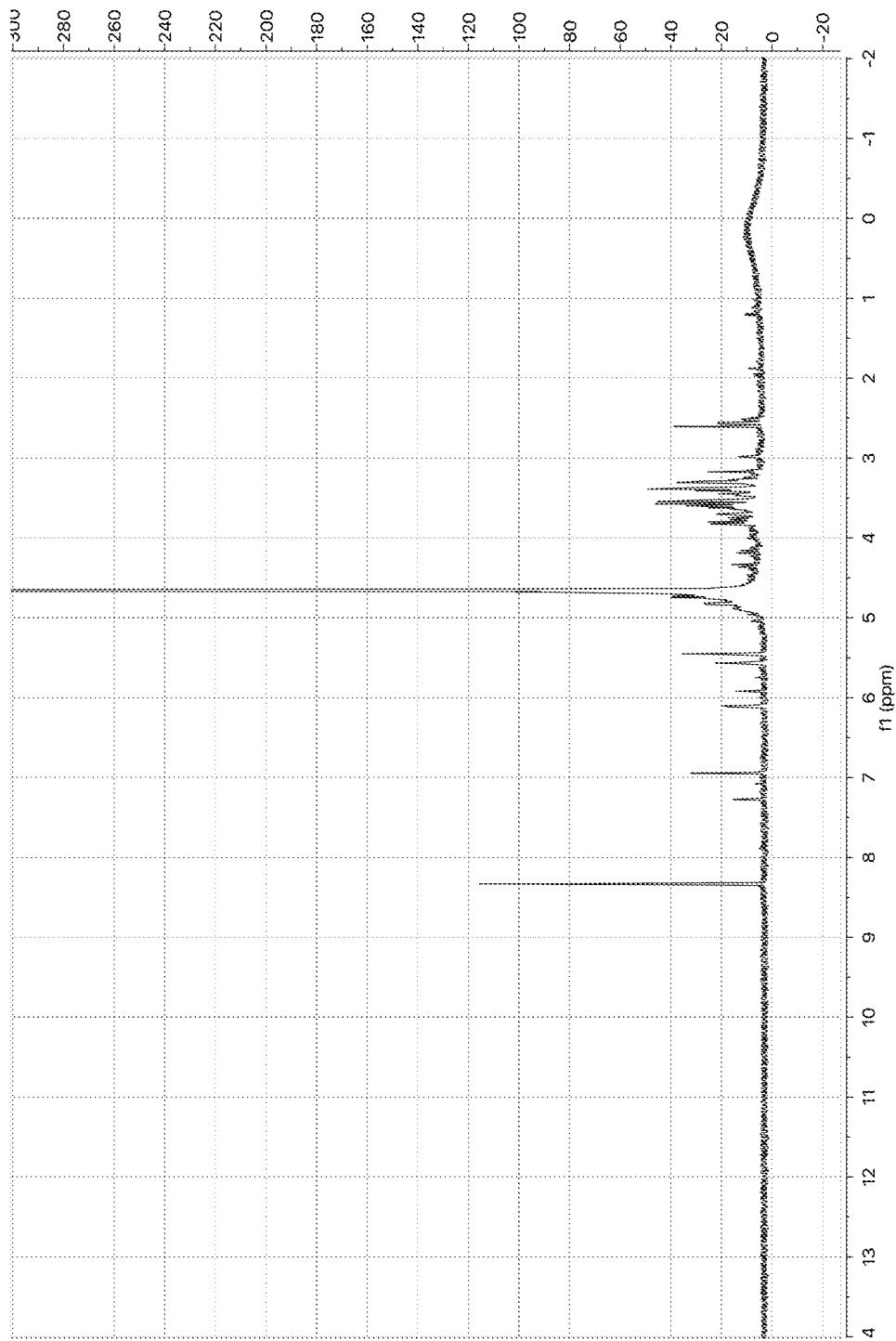
FIG. 9 shows the $^1$H NMR spectrum of iridoid 3 (500 MHz, $D_2O$), according to an embodiment of the present invention.

Another constituent of the antimicrobial compositions derived from cranberry, according to principles of the invention, is a terpene glycoside, preferably an iridoid (FIG. 2). In a preferred embodiment of the present invention, the terpene glycoside is a monotropein.

EXAMPLES

Cranberry hull was treated with pectinase (Klerzyme 150, DSM Food Specialties, South Bend, Ind., USA) before further purification by reverse-phase C18 flash chromatography using a CombiFlash Rf purification system (Teledyne ISCO, Inc., Lincoln, Nebr., USA). Briefly, 2 g pectinase treated cranberry material was loaded onto a RediSep GOLD C18 reverse-phase column (Teledyne ISCO, Inc., Lincoln, Nebr., USA) and eluted sequentially with deionized water, 15% methanol/water, and 500 mL methanol. Eluates were pooled and designated as Cranf1W (100% water eluate, 38.1%), Cranf1b (15% Methanol/water eluate, 23.8%), and Cranf1M (100% methanol eluate, 28.1%). The 15% Methanol/water eluted fraction, Cranf1b, was enriched in oligosaccharides.

The oligosaccharide constituents of Cranf1b were further purified using a porous graphitized carbon (PGC) solid phase extraction cartridge (1 gram, Thermo Scientific, Waltham, Mass., USA). The PGC cartridge was first conditioned by eluting with 50% acetonitrile/water and then equilibrated with deionized water. Cranf1b (20 mg) was loaded onto the cartridge and eluted first with 6 mL of deionized water and then sequentially eluted with 10% acetonitrile/water acidified with 0.1% trifluoroacetic acid (TFA) to obtain the pectic oligosaccharides and 30% acetonitrile/water acidified with 0.1% TFA to obtain the xyloglucan oligosaccharides. The structures of the oligosaccharides and terpene glycosides were determined using a combination of nuclear magnetic resonance (NMR) spectroscopy and mass spectrometry (MS) (FIGS. 3-9).

Figure 10:
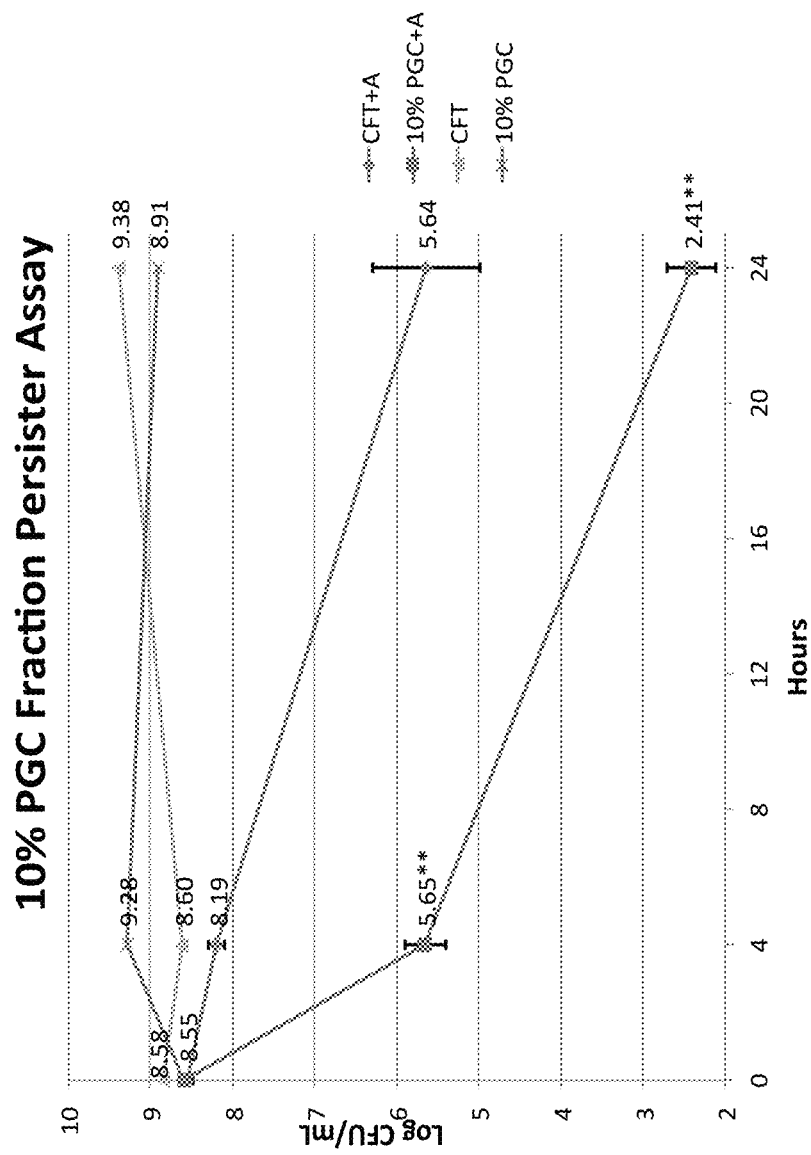
FIG. 10 is a graphical representation of the persister cell lowering effect from cranberry-derived compositions in a Persister Assay. The graph shows the effect of treating UPEC persister cells with ampicillin ("A") and pectic oligosaccharides containing terpene glycosides ("10% PGC"). The combination of ampicillin and the 10% PGC fraction (the "10% PGC+A" line, lowest in the graph) showed an approximately 3-log reduction in viable cells after 24 hours versus treatment with ampicillin alone (the "CFT+A" line). The cranberry component alone showed no significant antibiotic activity (the "10% PGC" line). Untreated UPEC cells served as the control ("CFT"). The UPEC in this experiment was *E. coli* CFT073 (**p=0.0001).

To examine the persister cell lowering-effect of the compositions derived from cranberry, pectic oligosaccharides containing terpene glycosides, purified as described above, were co-administered with antibiotics, e.g., a penicillin such as ampicillin to bacterial culture such as *E. coli* CFT073 bacterial culture (FIG. 10). In our experiments, CFT073 was cultured in 0.2% glucose M9 minimal media for 24 hours in the presence and absence of cranberry-derived compositions and ampicillin. Cultures were tested for bacterial viability (in log CFU/mL) at 0, 4, and 24 hours. The 24-hour time point is representative of the persister cell fraction.

When comparing the remaining persister cells at 24 hours in ampicillin-treated cultures with or without cranberry-derived compositions of the invention, we measured an average of an impressive 3.45 log CFU/mL reduction of persister cells when the cranberry fraction enriched with the oligosaccharides of the invention, i.e., enriched in both pectic and xyloglucan oligosaccharides, was included (p=0.0001). Comparable results, as described above in reference to FIG. 10, were obtained with the 10% PGC fraction, which contained a mixture of pectic oligosaccharides and terpene glycosides.

We also observe that when the cranberry-derived compositions were administered to the bacteria culture without ampicillin, cell viability remained above 9 log CFU/mL, showing that this is not an additive, but synergistic antibacterial effect.

Figure 11:
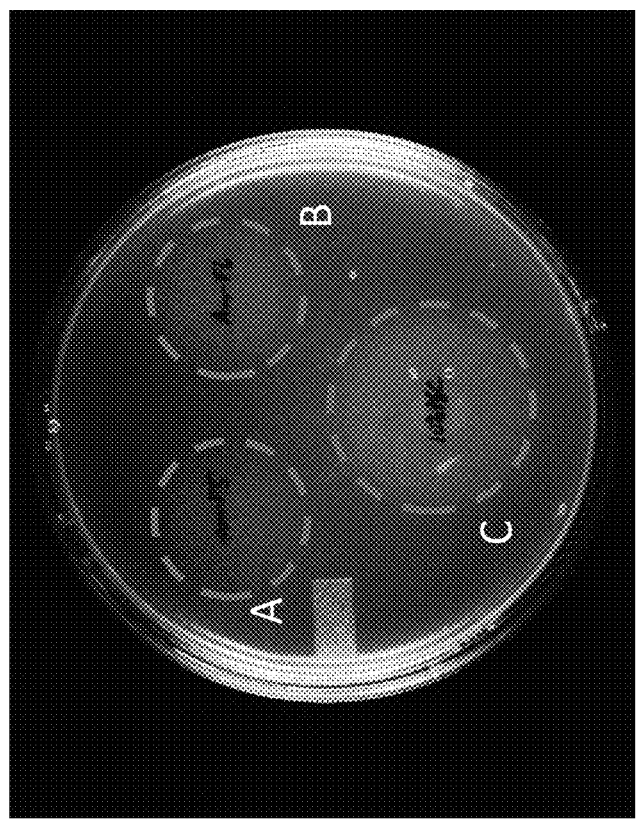
FIG. 11 is a photograph showing, respectively, effects of a substantially pure pectic oligosaccharide and two fractions of oligosaccharides on quiescent UPEC cell populations. Prevention of quiescence by a substantially pure pectic oligosaccharide (4-sugar units, u4$^3$) ("A"), a mixture of various pectic oligosaccharides ("B"), and the 10% PGC fraction, which mainly consists of pectic oligosaccharides and terpene glycosides ("C"). Bacteria growth was reactivated in the presence of all three of these test samples.

Referring now to FIG. 11, to examine possible prevention by the compositions of the present invention against the forming of quiescent cells, UPEC strain CFT073 was streaked from cryo stocks onto LB agar plates and incubated overnight at 37° C. A loopful of cells from the plate were added to 10 mL 0.4% glucose M9 minimal media in a 125 mL culture flask and incubated overnight at 37° C. and 200 rpm. Bacteria from this culture were diluted to a final concentration of $10^5$ CFU in 4 mL of liquid overlay media (0.2% glucose M9 minimal media with 0.9% noble agar at 45° C.). Each 4 mL overlay inoculum was poured over a pre-warmed (37° C.) 0.2% glucose M9 minimal media agar plate immediately after inoculation. These plates were allowed to solidify at room temperature with lids slightly ajar. Test samples were added to the overlay media and allowed to dry before incubating the plate upside down at 37° C. for 24 hours. To test prevention of quiescence, test samples were added immediately after the overlay media has solidified. A positive control (3 co-spots of 5 µL of each tyrosine, lysine, and methionine at 0.1 mg/mL) was used to observe prevention of quiescence.

Results shown in FIG. 11 indicate that a pure pectic oligosaccharide (4-sugar units, $u4^3$) ("A"), a mixture of pectic oligosaccharides ("B"), and the 10% PGC fraction ("C") which included a mixture of the oligosaccharides and terpene glycosides of the invention, can all prevent or inhibit quiescence in UPEC strain CFT073, as bacterial regrowth was observed for the UPEC strain ("reactivation") in the presence of each of these three samples.

While not wishing to be bound by any particular theory, we postulate that one or more of the compositions we derived from cranberry were able to sensitize the persister cells in the bacterial population, making them susceptible to antibiotic treatment, e.g., a bactericidal antibiotic. Moreover, the inhibition of quiescence in UPEC seen with the cranberry oligosaccharides could directly hinder the ability of the UPEC to establish a QIR, thereby reducing the likelihood of a recurrent UTI. Inhibitory effects on both persistence and quiescence, two distinct yet related factors contributing to pathogenic, especially recurrent, infections that we observed with the compositions of the invention support a wide range of antimicrobial applications. Accordingly, the compositions according to the principles of the present invention can be used in combination with a further antimicrobial treatment, such as an antibiotic, to potentiate the latter's bactericidal efficacy.

The cranberry-derived compositions can be administered prior to or simultaneously with the bactericide. The cranberry-derived compositions can be purified first before being mixed with a pharmaceutically acceptable excipient, carrier, or diluent, and made into a pharmaceutical or therapeutic for treating and/or preventing animal and human patients against pathogenic infections. The cranberry-derived compositions can be also made into cruder preparation or formulations for similar purposes, e.g., by mixing into an animal feed or antiseptic solution (e.g., for spraying).

The antibiotics that can be used in combination with the novel compositions derived from cranberry, to treat a patient suffering from a pathogenic (e.g., bacterial) infection therapeutically or prophylactically, include and are not limited to: Aminoglycosides (e.g., gentamicin and tobramycin), Beta-Lactams including Penicillins (e.g., penicillin, amoxicillin, and ampicillin) and Cephalosporins (e.g., cephalexin), Carbapenems (e.g., meropenem, imipenem, doripenem, biapenem, and tebipenem), Fluoroquinolones (e.g., ciprofloxacin, levofloxacin, and ofloxacin), Sulfonamides (e.g., co-trimoxazole, and trimethoprim), Macrolides (e.g., erythromycin, clarithromycin, and azithromycin), and Tetracyclines (e.g., tetracycline, and doxycycline).

Besides antibiotics, other bactericide that can be used in combination with embodiments of the invention include antiseptics and disinfectants, e.g., various chlorine preparations, peroxides, iodine preparations, alcohols, weak organic acids, cationic surfactants, phenolic substances, heavy metals (e.g., silver and copper), and so on.

The compositions described herein according to principles of the invention can be used to treat a variety of conditions and diseases linked to bacterial infection, such as those caused by gram-negative or gram-positive bacteria. Examples of such infections include and are not limited to those known to exhibit persister cell phenotypes: *Staphylococcus aureus, Escherichia coli, Pseudomonas aeruginosa, Lactobacillus acidophilus*, and *Gardnerella vaginalis*. Recurrent bacterial infections that can be treated with the compositions of the invention include and are not limited to: Urinary Tract Infections (UTIs), bacteremia, staphylococcal endocarditis, pneumonia, tuberculosis, and biofilm-associated infections such as those in cystic fibrosis.

The term "pharmaceutically acceptable excipient, carrier, or diluent" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

While the present invention has been particularly shown and described with reference to the structure and methods disclosed herein and as illustrated in the drawings, it is not confined to the details set forth and this invention is intended to cover any modifications and changes as may come within the scope and spirit of the following claims. All publications and patent literature described herein are incorporated by reference in entirety to the extent permitted by applicable laws and regulations.

We claim:

1. A composition that induces bacteria out of their dormant state before killing them, comprising a pectic oligosaccharide as an active ingredient and an antimicrobial selected from the group consisting of an antibiotic, an antiseptic, and a disinfectant, wherein the pectic oligosaccharide comprises an oligomer of poly-galacturonic acid with 4 to 8 repeating galacturonic acid units, and having at least one carboxylic acid side chain or esterified side chain on each of the galacturonic acid unit; and wherein the composition is capable of and effective in making a population of bacterial persister or quiescent cells susceptible to further antimicrobial treatment after inducing them out of their dormant state.

2. The composition of claim 1, wherein the antibiotic is bactericidal.

3. The composition of claim 1, wherein the antibiotic is selected from the group consisting of Aminoglycosides, Penicillins, Cephalosporins, Carbapenems, Fluoroquinolones, Sulfonamides, Macrolides, and Tetracyclines.

4. The composition of claim 1, wherein the antibiotic is selected from the group consisting of gentamicin, tobramycin, penicillin, amoxicillin, ampicillin, cephalexin, meropenem, imipenem, doripenem, biapenem, tebipenem, ciprofloxacin, levofloxacin, ofloxacin, co-trimoxazole, trimethoprim, erythromycin, clarithromycin, azithromycin, tetracycline, and doxycycline.

5. The composition of claim 1, wherein the pectic oligosaccharide has at least one unsaturated carbon bond.

6. The composition of claim 1, in a form selected from the group consisting of a powder, a gel, a vapor, a fluid, and a combination thereof.

7. The composition of claim 1, wherein the pectic oligosaccharide comprises a poly-galacturonic acid with four galacturonic acid units.

8. The composition of claim 1, wherein the pectic oligosaccharide comprises a poly-galacturonic acid that is modified in that one or more of the carboxylic acid side chains are methyl esterified.

9. The composition of claim 1, wherein one or more of the hydroxyl groups in the pectic oligosaccharide are acetylated.

10. The composition of claim 1, wherein the poly-galacturonic acid can be represented in formula as follows:

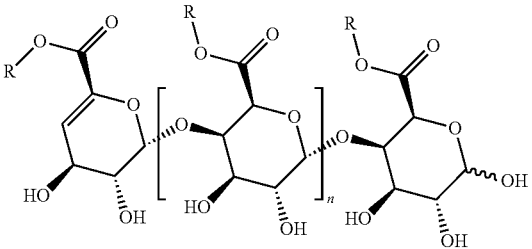

where each R is independently $CH_3$ or H, and n=2, 3, 4, 5, or 6.

11. The composition of claim 10, wherein the poly-galacturonic acid can be represented in formula as follows:

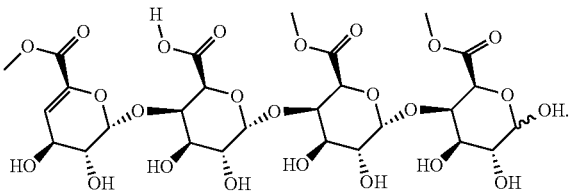

12. A composition comprising a bactericidal antibiotic and a preparation of a pectic oligosaccharide comprising an oligomer of poly-galacturonic acid with a degree of polymerization selected from the group of integers consisting of 4, 5, 6, 7, and 8, and having at least one carboxylic acid or esterified side chain on each of the galacturonic acid unit.

* * * * *